(12) United States Patent
Wang (10) Patent No.: US 9,675,240 B2
(45) Date of Patent: Jun. 13, 2017

(54) MOUTH MIRROR APPARATUS

(71) Applicant: Sheng-Peng Wang, Taipei (TW)

(72) Inventor: Sheng-Peng Wang, Taipei (TW)

(*) Notice: Subject to any disclaimer, the term of this patent is extended or adjusted under 35 U.S.C. 154(b) by 0 days.

(21) Appl. No.: 14/935,019

(22) Filed: Nov. 6, 2015

(65) Prior Publication Data

US 2016/0360957 A1 Dec. 15, 2016

(30) Foreign Application Priority Data

Jun. 11, 2015 (TW) .............................. 104118917 A (51) Int. Cl.
*A61B 1/253* (2006.01)
*A61C 17/06* (2006.01)
*A61C 1/00* (2006.01)

(52) U.S. Cl.
CPC ............ *A61B 1/253* (2013.01); *A61C 1/0069* (2013.01); *A61C 1/0092* (2013.01); *A61C 17/043* (2013.01)

(58) Field of Classification Search
CPC ................................. A61B 1/126; A61B 1/253
See application file for complete search history.

(56) References Cited

U.S. PATENT DOCUMENTS

| 3,859,987 | A | * | 1/1975 | Holstad ................. | A61B 1/253 433/30 |
| 4,261,637 | A | * | 4/1981 | King ..................... | A61B 1/253 359/508 |
| 4,408,991 | A | | 10/1983 | Engel | |
| 5,449,290 | A | | 9/1995 | Reitz | |
| 6,247,924 | B1 | * | 6/2001 | Gunnarsson .......... | A61B 1/253 433/30 |
| 6,575,744 | B1 | | 6/2003 | Oshida | |

FOREIGN PATENT DOCUMENTS

| CH | 364 866 A | 10/1962 |
| CN | 1883373 A | 12/2006 |
| DE | 28 44 774 A1 | 4/1979 |
| EP | 2 181 643 A1 | 5/2010 |

OTHER PUBLICATIONS

Search Report issued in counterpart European Application No. 15197220.5, Nov. 8, 2016.

* cited by examiner

*Primary Examiner* — Ralph Lewis
(74) *Attorney, Agent, or Firm* — Hamre, Schuman, Mueller & Larson, P.C.

(57) ABSTRACT

A mouth mirror apparatus is adapted to be connected to a suction device and includes a mounting frame, an elongated handle, and a mirror member. The mirror member is rotatably mounted on a major wall of the mounting frame and can be driven to rotate when the suction device is actuated. When the mirror member rotates, a centrifugal force is generated to fling off water drops and/or debris on a reflecting surface of the mirror member.

9 Claims, 7 Drawing Sheets

MOUTH MIRROR APPARATUS

CROSS-REFERENCE TO RELATED APPLICATION

This application claims priority from Taiwanese application no. 104118917, filed on Jun. 11, 2015.

FIELD

The disclosure relates to a mouth mirror apparatus, more particularly to a mouth mirror apparatus adapted to be connected to a suction device.

BACKGROUND

U.S. Pat. No. 5,449,290 discloses a dental mirror which has an airflow bore therein to direct an airflow onto a surface of a mirror to dissipate mist or debris generated inside the patient's mouth during a procedure. The dental mirror consists of threadably engaged mirror and handle sections, to allow for cleaning and sterilisation of the instrument.

SUMMARY

An object of the disclosure is to provide a novel mouth mirror apparatus, which allows for easy removal of mist, water drops, or debris from a reflective surface of a mouth mirror.

According to the disclosure, a mouth mirror apparatus includes a mounting frame, an elongated handle, and a mirror member. The mounting frame defines a central axis, and includes a major wall with a periphery, and a surrounding wall which has upper and lower wall segments. The upper wall segment extends upwardly from the periphery to surround the central axis and to terminate at an upper end, and defines an upper space together with the major wall. The upper wall segment has a suction port. The lower wall segment extends downwardly from the periphery to surround the central axis and to terminate at a lower end, and defines a lower space together with the major wall. The elongated handle defines therein a passage, and has a fluid outlet port downstream of the passage. The elongated handle is connected to the surrounding wall such that the passage is disposed downstream of the suction port. The mirror member is rotatably mounted on the major wall, and includes a mirror body which is disposed in the upper space and which has a reflecting surface facing upwardly, and a rotatable shaft which extends downwardly from the mirror body through the major wall into the lower space so as to be driven to rotate about a shaft axis.

BRIEF DESCRIPTION OF THE DRAWINGS

Other features and advantages of the disclosure will become apparent in the following detailed description of the embodiments with reference to the accompanying drawings, in which.

DETAILED DESCRIPTION

Before the disclosure is described in greater detail, it should be noted that like elements are denoted by the same reference numerals throughout the disclosure.

Figure 1:
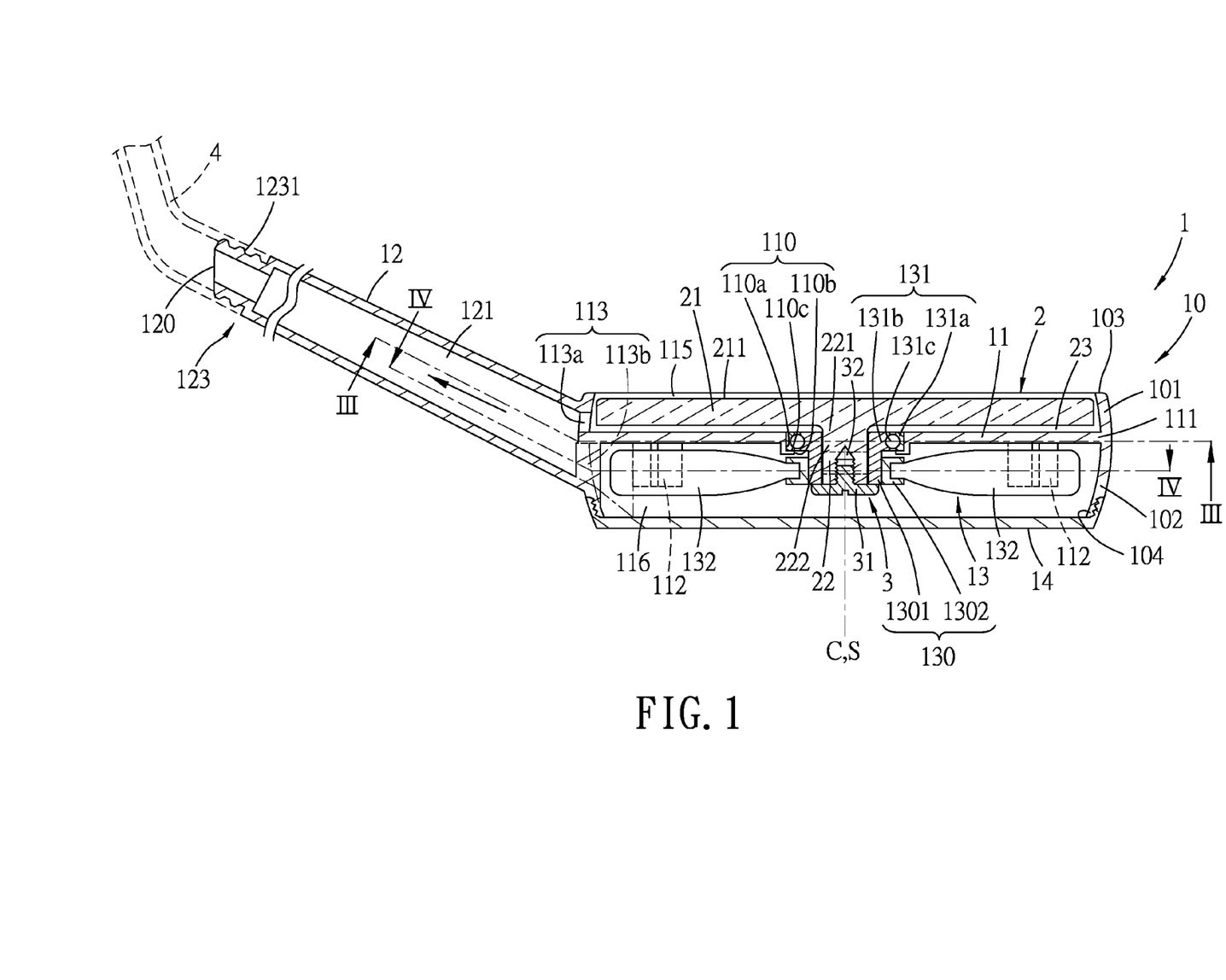
FIG. 1 is a cross-sectional view of a mouth mirror apparatus according to a first embodiment of the disclosure.

With reference to FIG. 1, a mouth mirror apparatus according to a first embodiment of the disclosure includes a mounting frame 1, an elongated handle 12, a mirror member 2, a driving member 13, a bearing unit 131, and a fastening member 3. The mouth mirror apparatus is adapted to be connected to a suction device (not shown), such as a pump, by means of a silicon rubber tube 4.

The mounting frame 1 defines a central axis (C), and includes a surrounding wall 10, a major wall 11 with a periphery 111, and a bottom cover wall 14.

The surrounding wall 10 has upper and lower wall segments 101, 102. The upper wall segment 101 extends upwardly from the periphery 111 of the major wall 11 to surround the central axis (C) and to terminate at an upper end 103. The upper wall segment 101 defines an upper space 115 together with the major wall 11, and has a suction port (113*a*) in fluid communication with the upper space 115. The lower wall segment 102 extends downwardly from the periphery 111 to surround the central axis (C) and to terminate at a lower end 104. The lower wall segment 102 defines a lower space 116 together with the major wall 11.

The major wall 11 has a through hole 110 which includes a larger diameter upper hole section (110*a*) and a smaller diameter lower hole section (110*b*). The smaller diameter lower hole section (110*b*) and the larger diameter upper hole section (110*a*) define a shoulder surface (110*c*) therebetween.

The bottom cover wall 14 is secured to the lower end 104 of the lower wall segment 102 to enclose the lower space 116. In this embodiment, the bottom cover wall 14 is detachably and threadedly secured to the lower end 104 of the lower wall segment 102.

The elongated handle 12 defines therein a passage 121, and has a fluid outlet port 120 downstream of the passage 121. The elongated handle 12 is connected to the surrounding wall 10 such that the passage 121 is disposed downstream of the suction port (113*a*). In this embodiment, the elongated handle 12 includes a tubular end portion 123 which defines the fluid outlet port 120, and which has a serrated outer surface 1231 so as to be in friction engagement with an inner surface of the silicon rubber tube 4. The fluid outlet port 120 is configured to face downwardly. With the arrangement of the serrated outer surface 1231, the tubular end portion 123 of the elongated handle 12 is less likely to disengage from the silicon rubber tube 4 is use.

Figure 2:
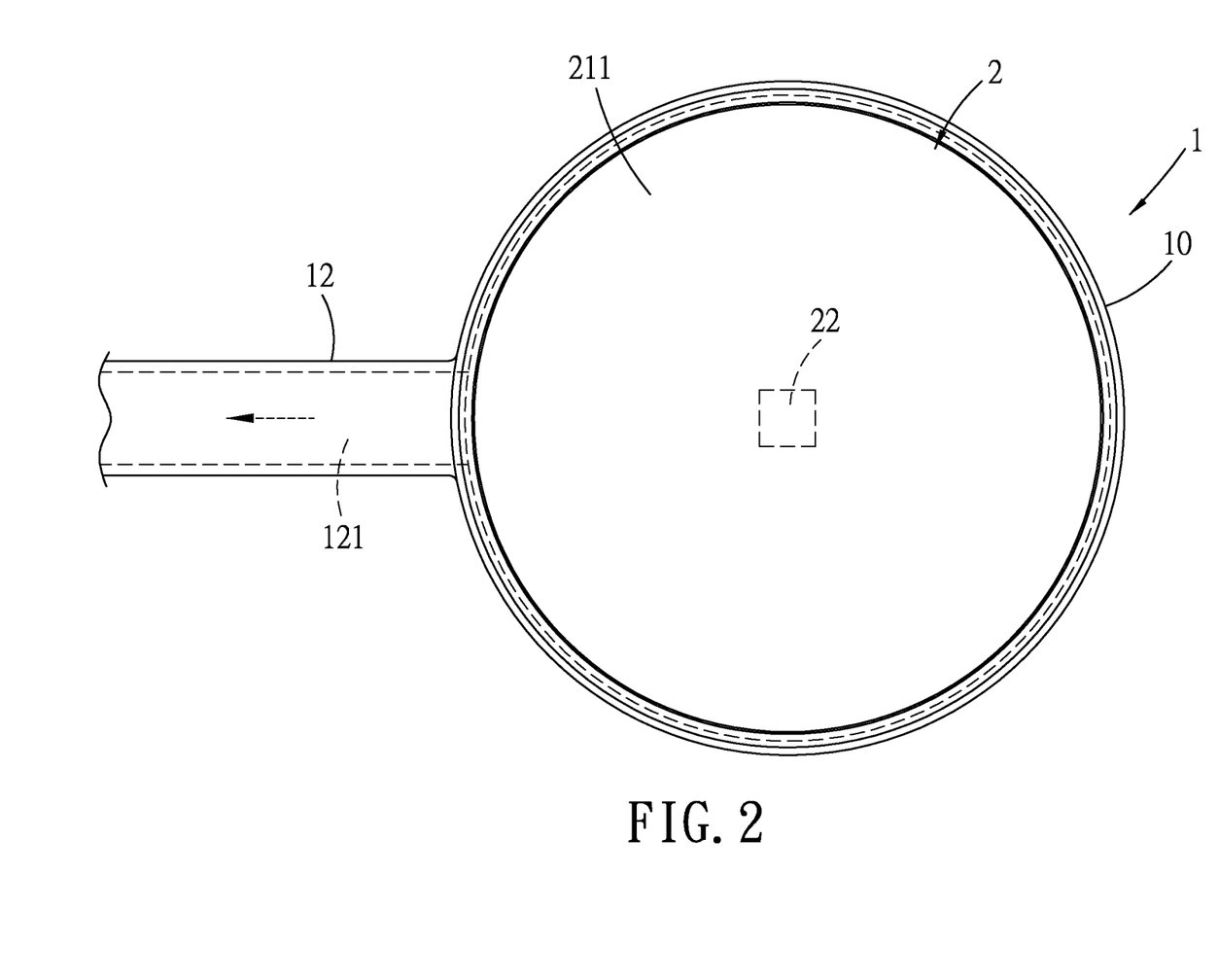
FIG. 2 is a fragmentary schematic top view of the mouth mirror apparatus.
Figure 3:
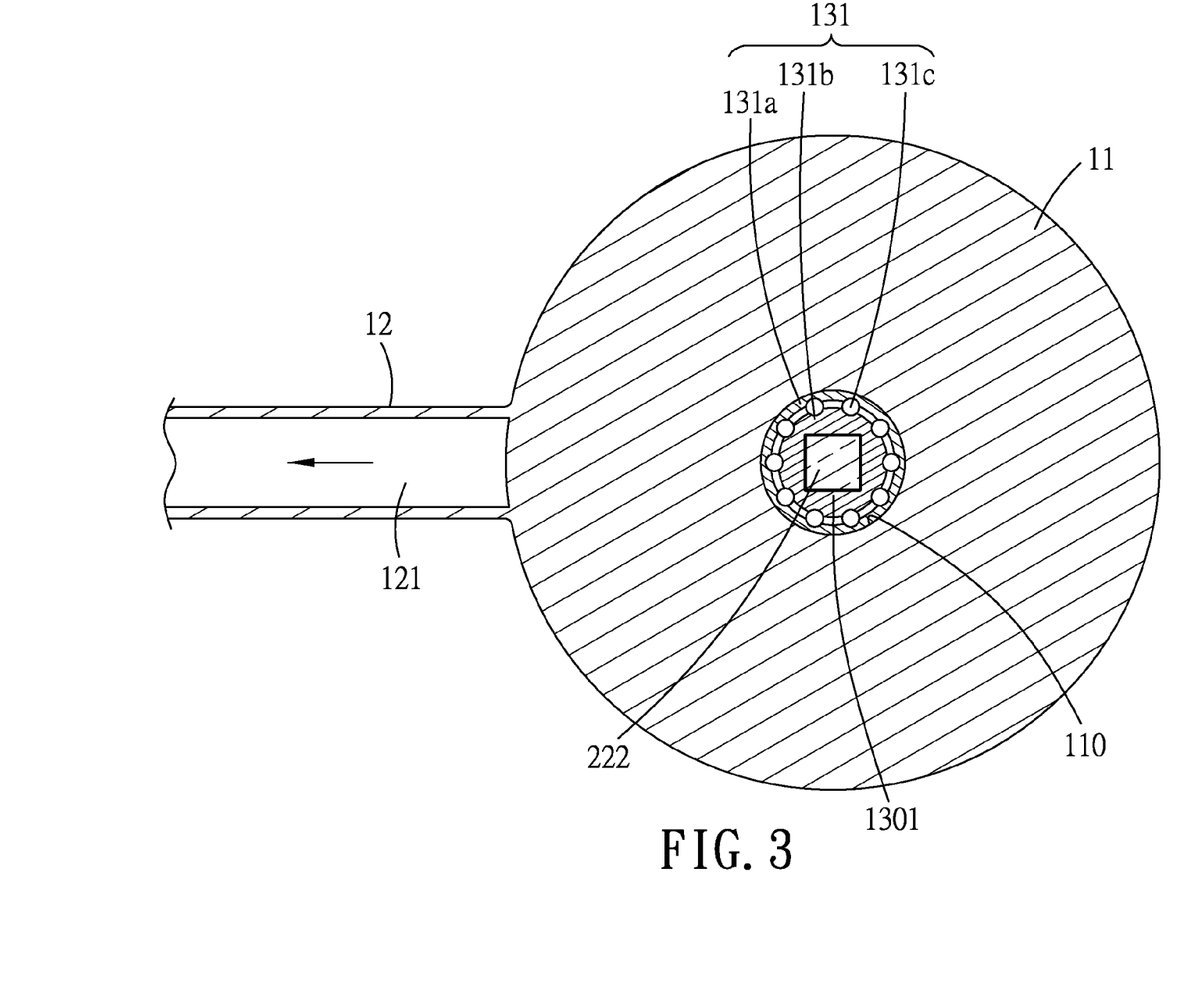
FIG. 3 is a fragmentary cross-sectional view taken along line III-III of FIG. 1.

The mirror member 2 is rotatably mounted on the major wall 11, and includes a mirror body 21 and a rotatable shaft 22. The mirror body 21 is disposed in the upper space 115, is spaced apart from the upper wall segment 101, and has a reflecting surface 211 which faces upwardly and which has a peripheral margin disposed beneath the upper end 103 of the upper wall segment 101. The rotatable shaft 22 extends downwardly from the mirror body 21 through the through hole 110 in the major wall 11 into the lower space 116 so as to be driven to rotate about a shaft axis (S). The shaft axis (S) is coaxial with the central axis (C). In this embodiment, the mirror member 2 is detachably mounted on the major wall 11. Thus, when the reflecting surface 211 is damaged, it is only necessary to remove the mirror member 2 from the major wall 11 and then mount a new mirror member 2 on the major wall 11. The rotatable shaft 22 is a non-cylindrical shaft (see FIGS. 2 to 4) and has a quadrilateral cross-section. In other embodiments, the rotatable shaft 22 may nave a semicircular cross-section, a hexagonal cross-section, an octagonal cross-section, etc. Referring back to FIG. 1, the rotatable shaft 22 is shown to have large and small dimension sections 221, 222 which are proximate to and distal from the mirror body 21, respectively. As such, the mirror body 21 is disposed to be spaced apart from the major wall 11.

The driving member 13 is coupled to the rotatable shaft 22 so as to drive the rotatable shaft 22 to rotate about the shaft axis (S). In this embodiment, the driving member 13 is rotatably disposed in the lower space 116 and is mounted on the rotatable shaft 22 so as to permit the rotatable shaft 22 to rotate therewith. The driving member 13 includes a hub 130 and a plurality of blades 132. The hub 130 has a hub body 1301 and a flange 1302. The hub body 1301 is sleeved on the rotatable shaft 22 and extends through the through hole 110 into the lower space 116. The flange 1302 extends radially from the hub body 1301 and is disposed downwardly of the major wall 11. The blades 132 are mounted on the flange 1302 of the hub 130 and are angularly displaced from one another about the shaft axis (S).

The bearing unit 131 is disposed in the through hole 110 of the major wall 11, on the shoulder surface (110c), and between the major wall 11 and the hub 130 to permit the hub 130 to rotate relative to the major wall 11. The bearing unit 131 includes an outer race (131a), an inner race (131b), and antifriction members (131c) (such as antifriction balls). The outer race (131a) is fixed to the major wall 11. The inner race (131b) and the hub body 1301 are integrally formed in one piece. The antifriction members (131c) are sealed between the outer race (131a) and the inner race (131b) to avoid contact with air or liquid. In this embodiment, the hub body 1301 of the hub 130 is matingly engaged with the small dimension section 222 of the rotatable shaft 32, and the large dimension section 221 is disposed between the hub 130 and the mirror body 21 so as to permit the mirror body 21 to be spaced apart from the major wall 11 by a gap 23 to thereby prevent the mirror body 21 from contacting the major wall 11 during rotation of the mirror member 2.

The fastening member 3 is removably connected to the rotatable shaft 22, and has an abutment head 31 and a threaded shank 32 such that when the threaded shank 32 is screwed into the rotatable shaft 22 along the shaft axis (S), the abutment head 31 is brought into abutting engagement with both the hub 130 and the rotatable shaft 22 to thereby permit co-rotation of the driving member 13 and the mirror member 2. In addition, when the threaded shank 32 of the fastening member 3 is screwed into the rotatable shaft 22, the upper space 115 and the lower space 116 are not in fluid communication with each other via the through hole 110.

Figure 4:
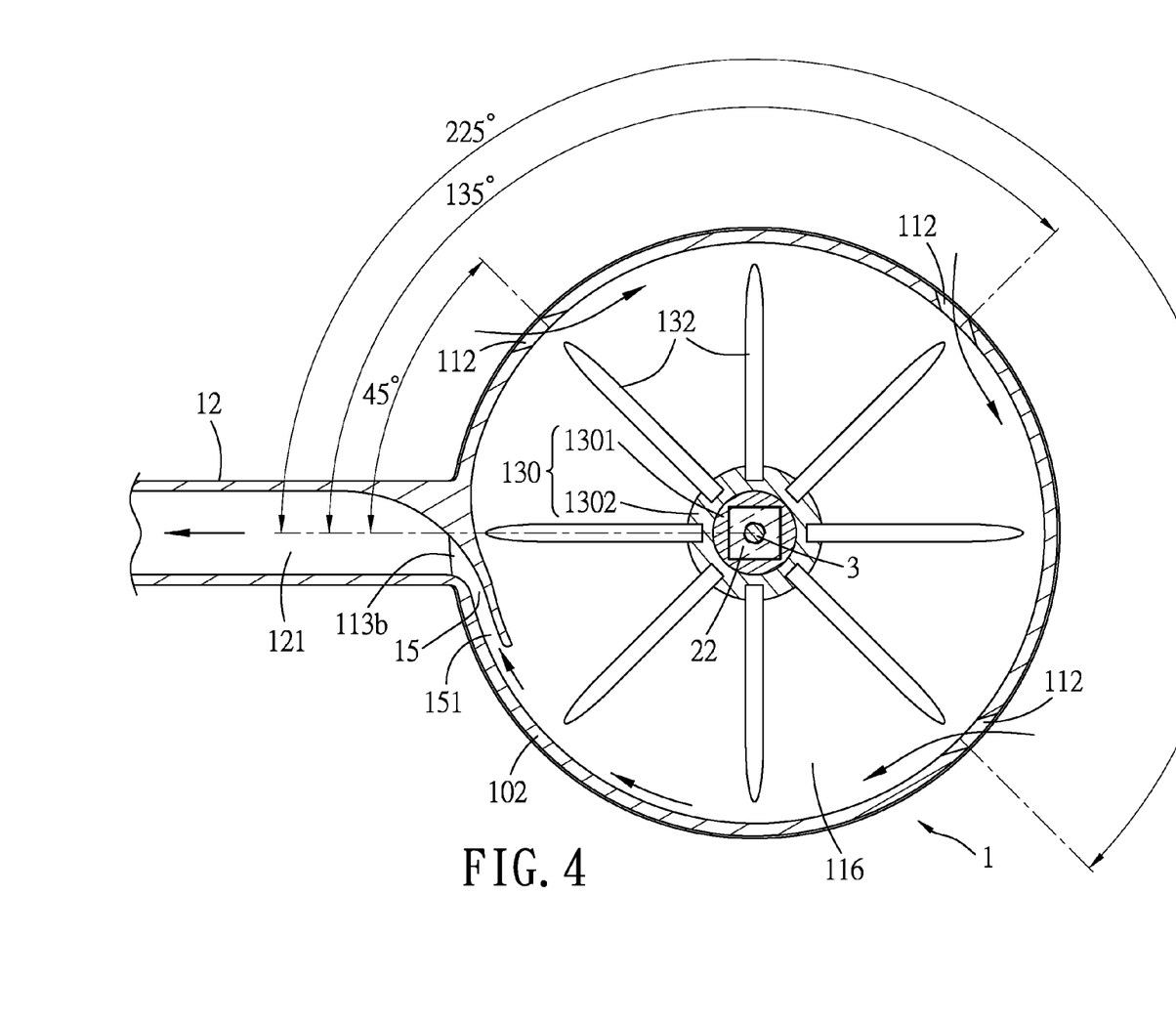
FIG. 4 is a fragmentary cross-sectional view taken along line IV-IV of FIG. 1.
Figure 5:
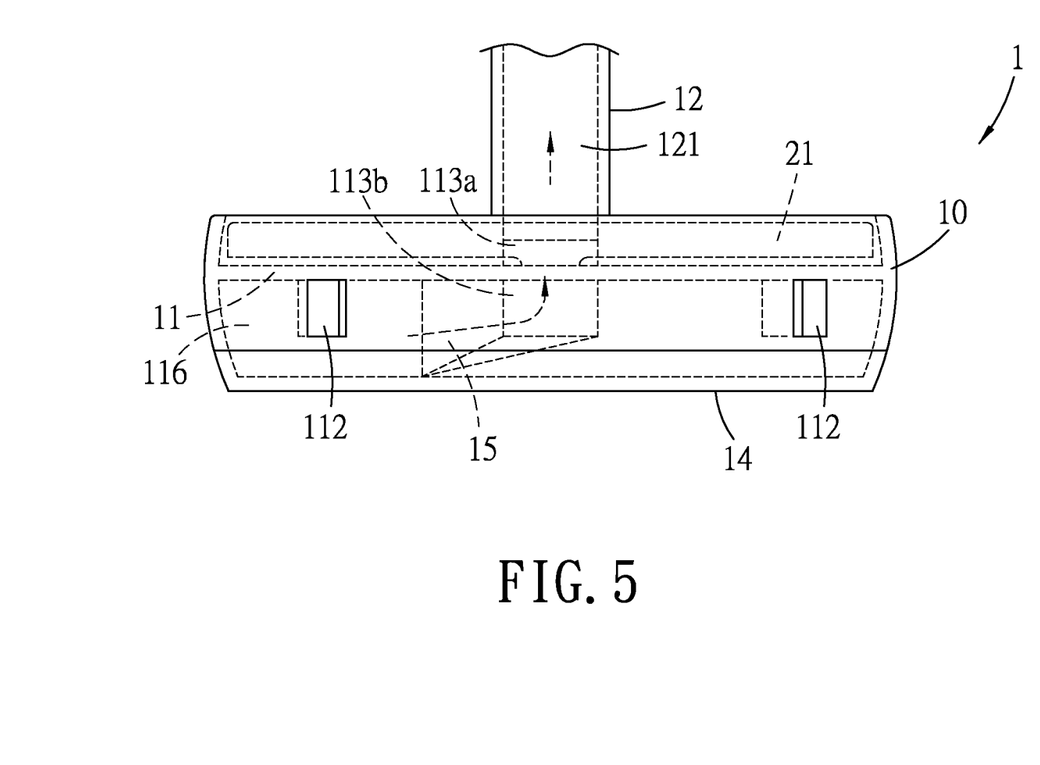
FIG. 5 is a fragmentary schematic side view of the mouth mirror apparatus.

As best shown in FIG. 4, the lower wall segment 102 has an internal port (113b) and the mounting frame 1 is formed with at least one fluid intake port 112. The internal port (113b) communicates the passage 121 with the lower space 116. The fluid intake port 112 is disposed upstream of the internal port (113b) such that, by a suction force provided by the section device, a fluid stream is permitted to be drawn into the lower space 116 through the fluid intake port 112 to flow toward the internal port (113b) so as to force the blades 132 to rotate about the shaft axis (S) to thereby rotate the mirror member 2. The fluid stream, may include air and/or liquid and may also carry debris generated during dental procedures. As shown in FIGS. 1 and 4, the fluid intake port 112 is formed in the lower wall segment 102 and is inclined at an angle so as to permit the fluid stream in the lower space 116 to flow in a clockwise direction along the lower wall segment 102 (see FIG. 4).

The fluid intake port 112 can be varied in number depending on design requirements. In this embodiment, the lower wall segment 102 has three fluid intake ports 112. An angle between the internal port (113b) and each of the fluid intake ports 112 relative to the central axis (C) or the shaft axis (S) is about 45°, 135°, or 225°(see FIGS. 1 and 4). For the sake of description, the three fluid intake ports 112 are referred to hereinafter as a port at 45°, a port at 135°, and a port at 225°. When the mouth mirror apparatus is held by a left hand of a dentist to gain better visualization of the teeth, the port 112 at 45° is on the upper side, the port 112 at 135° is substantially opposite the elongated handle 12, and the port 112 at 225° is on the lower side for drawing out excess saliva or water during dental procedures.

Furthermore, the mounting frame 1 further includes a channel 15 which is disposed upstream of the internal port (113b), and which extends from the infernal port (113b) along the lower wall segment 102 to terminate at an entry port 151 which is disposed to ensure that the fluid stream flows along the lower wall segment 102 into the channel 15.

Because the lower space 116 is almost an enclosed space except where it communicates with the internal port 113b and the fluid intake ports 112, and because of the inclined configuration of the channel 15 and the fluid intake ports 112, the fluid stream can be steadily generated and is sufficient to drive the blades 132 to rotate to thereby rotate the mirror member 2.

When the mirror member 2 rotates, a centrifugal force is generated to fling off water drops and/or debris on the reflecting surface 211, and the fluid in the upper space 115 can be drawn outwardly through the suction port (113a) and the passage 121 by virtue of the suction force of the suction device. In addition, when the suction device is operated, a suction pressure is exerted on the reflecting surface 211 through the suction port (113a). Thus, the reflecting surface 211 is less likely to fog up, and the mist on the reflecting surface 211, if any, can also be dissipated.

In this embodiment, because the mirror member 2 is driven to rotate by virtue of the fluid stream, it can be immediately stopped once the reflecting surface 211 of the mirror member 2 is in contact with, fox example, the tongue or teeth of a patient. In addition, because the mirror member 2 in this embodiment is not connected to an electrical power source, there is no risk of an electric shock.

It should be noted that although the mirror member 2 in this embodiment is driven by the fluid stream, in other embodiments, the mirror member 2 may be driven by, for example, electric power.

Moreover, the mouth mirror apparatus can be disassembled for cleaning and sterilization. To remove the mirror member 2, the bottom cover wall 14 is removed from the lower wall segment 102 of the surrounding wall 10, and the fastening member 3 is loosened. Then a pointed object such as a pin is inserted into a hole of the hub 130 to push the rotatable shaft 22 upwardly so that the mirror member 2 can be removed.

Figure 6:
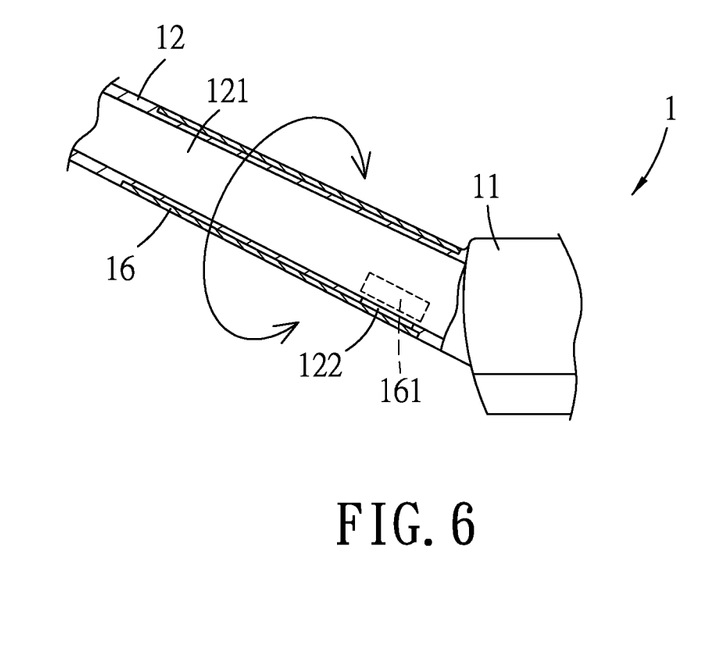
FIG. 6 is a fragmentary cross-sectional view of a mouth mirror apparatus according to a second embodiment of the disclosure.

FIG. 6 shows a part of a mouth mirror apparatus according to a second embodiment of the disclosure. The second embodiment is similar to the first embodiment except that, in the second embodiment, the elongated handle 12 is formed with an opening 122 which is in fluid communication with the passage 121, and which is disposed downstream of the internal port 113b (see FIG. 4). Furthermore, in the second embodiment, the mouth mirror apparatus further includes a gate member 16 which is mounted on the elongated handle 12, and which is displaceable between a closed position, where the opening 122 is closed by the gate member 16 to permit generation of the fluid stream, and an open position, where the opening 122 is open to interrupt the drawing of the fluid through the fluid intake ports 112.

In the second embodiment, the gate member 16 is a sleeve which is rotatably sleeved on the elongated handle 12, and which has a through bore 161. When the gate member 16 is displaced to the open position, the through bore 16 is in register with the opening 122. In other embodiments, the gate member 16 may be a slidable cover.

In addition, the opening 122 may have a dimension larger than that of each fluid intake port 112. When there is too much liquid (saliva and/or water) in a patient's mouth, the dentist, can displace the gate member 16 to the open position so as to facilitate removal of the liquid.

Figure 7:
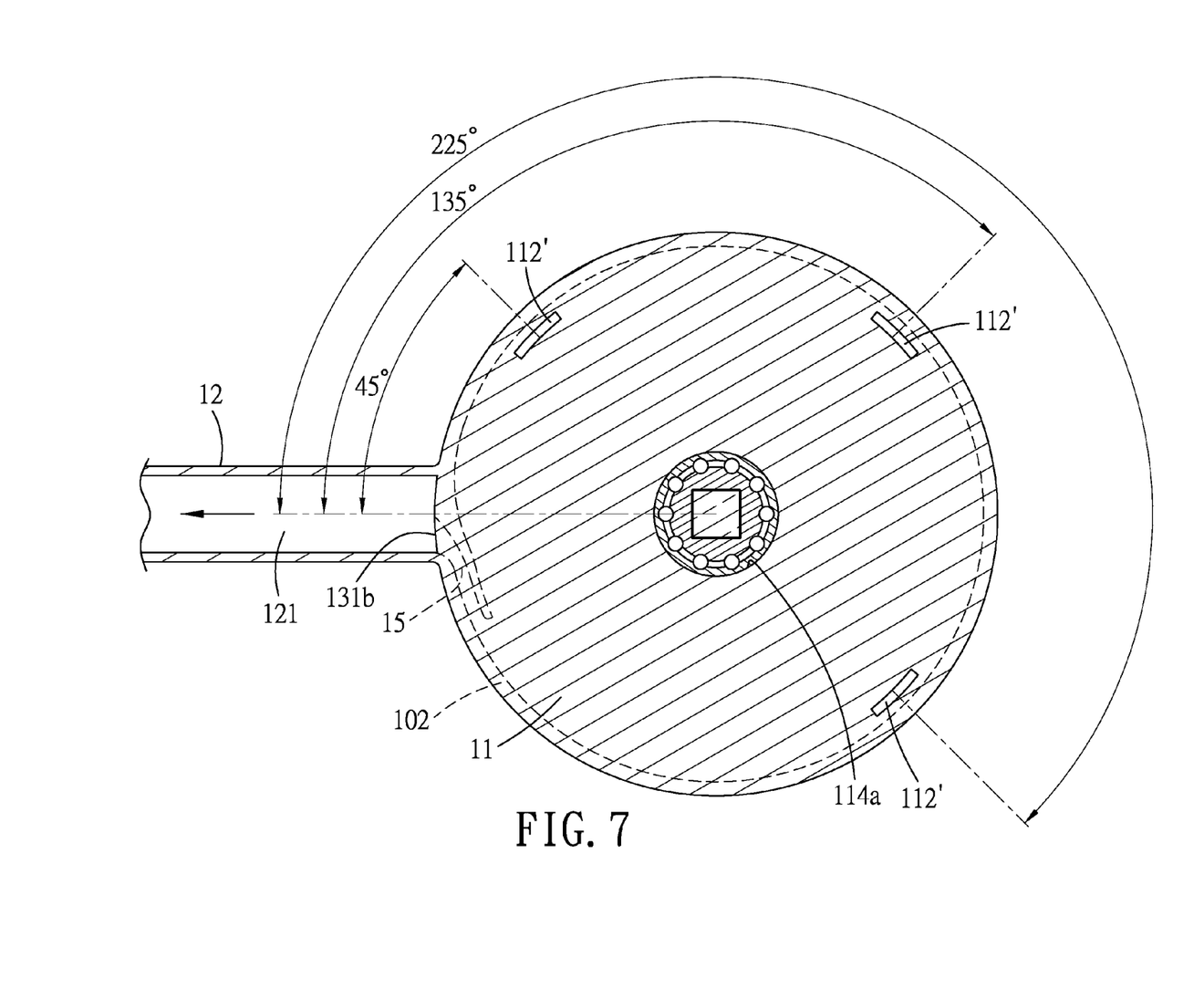
FIG. 7 is a fragmentary cross-sectional view of a mouth mirror apparatus according to a third embodiment of the disclosure.

FIG. 7 shows a part of a mouth mirror apparatus according to a third embodiment of the disclosure. The third embodiment is similar to the first embodiment except that, in the third embodiment, each of the three fluid intake ports 112' is formed in the major wall 11 and is disposed adjacent to the periphery 111 of the major wall 11 so as to permit the fluid stream to flow along the lower wall segment 102. In this embodiment, an angle between the internal port 113b and each of the fluid intake ports 112 relative to the central axis (C) or the shaft axis (S) (the central axis (C) and the shaft axis (S) are shown in FIG. 1) is about 45°, 135°, or 225°.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A mouth mirror apparatus comprising:
   a mounting frame defining a central axis, and including a major wall with a periphery, and a surrounding wall which has
      an upper wall segment which extends upwardly from said periphery to surround the central axis and to terminate at an upper end, and which defines an upper space together with said major wall, said upper wall segment having a suction port, and
      a lower wall segment which extends downwardly from said periphery to surround the central axis and to terminate at a lower end, and which defines a lower space together with said major wall;
   an elongated handle defining therein a passage, and having a fluid outlet port downstream of said passage, said elongated handle being connected to said surrounding wall such that said passage is disposed downstream of said suction port;
   a mirror member rotatably mounted on said major wall, and including a mirror body which is disposed in said upper space and which has a reflecting surface facing upwardly, and a rotatable shaft which extends downwardly from said mirror body through said major wall into said lower space so as to be driven to rotate about a shaft axis; and
   a driving member coupled to said rotatable shaft so as to drive said rotatable shaft to rotate about the shaft axis, said driving member being rotatably disposed in said lower space and being mounted on said rotatable shaft so as to permit said rotatable shaft to rotate therewith, said driving member including a plurality of blades which are angularly displaced from one another about the shaft axis, wherein
   said mounting frame further includes a bottom cover wall secured to said lower end of said lower wall segment to enclose said lower space, said lower wall segment having an internal port communicating said passage with said lower space, said mounting frame being formed with at least one fluid intake port disposed upstream of said internal port such that a fluid stream is permitted to be drawn into said lower space through said fluid intake port to flow toward said internal port so as to force said blades to rotate about the shaft axis to thereby rotate said mirror member.

2. The mouth mirror apparatus according to claim 1, wherein said mirror member is detachably mounted on said major wall.

3. The mouth mirror apparatus according to claim 1, wherein said fluid intake port is formed in said lower wall segment and is inclined at an angle so as to permit the fluid stream to flow along said lower wall segment.

4. The mouth mirror apparatus according to claim 1, wherein said fluid intake port is formed in said major wall and is disposed adjacent to said periphery of said major wall so as to permit the fluid stream to flow along said lower wall segment.

5. The mouth mirror apparatus according to claim 1, wherein said mounting frame further includes a channel which is disposed upstream of said internal port, and which extends from said internal port along said lower wall segment to terminate at an entry port which is disposed to ensure that the fluid stream flows along said lower wall segment into said channel.

6. A mouth mirror apparatus comprising:
   a mounting frame defining a central axis, and including a major wall with a periphery, and a surrounding wall which has
   an upper wall segment which extends upwardly from said periphery to surround the central axis and to terminate at an upper end, and which defines an upper space together with said major wall, said upper wall segment having a suction port, and
   a lower wall segment which extends downwardly from said periphery to surround the central axis and to terminate at a lower end, and which defines a lower space together with said major wall;
   an elongated handle defining therein a passage, and having a fluid outlet port downstream of said passage, said elongated handle being connected to said surrounding wall such that said passage is disposed downstream of said suction port;
   a mirror member rotatably mounted on said major wall, and including a mirror body which is disposed in said upper space and which has a reflecting surface facing upwardly, and a rotatable shaft which extends downwardly from said mirror body through said major wall into said lower space so as to be driven to rotate about a shaft axis;

a driving member coupled to said rotatable shaft so as to drive said rotatable shaft to rotate about the shaft axis, wherein said driving member is rotatably disposed in said lower space and is mounted on said rotatable shaft so as to permit said rotatable shaft to rotate therewith, said driving member including a plurality of blades which are angularly displaced from one another about the shaft axis;

wherein said mounting frame further includes a bottom cover wall secured to said lower end of said lower wall segment to enclose said lower space, said lower wall segment having an internal port communicating said passage with said lower space, said mounting frame being formed with at least one fluid intake port disposed upstream of said internal port such that a fluid stream is permitted to be drawn into said lower space through said fluid intake port to flow toward said internal port so as to force said blades to rotate about the shaft axis to thereby rotate said mirror member; and wherein said bottom cover wall is detachably secured to said lower end of said lower wall segment.

7. The mouth mirror apparatus according to claim 6, wherein said driving member further has a hub, on which said blades are mounted, said hub being sleeved on said rotatable shaft, said major wall having a through hole which includes a larger diameter upper hole section and a smaller diameter lower hole section, said smaller diameter lower hole section and said larger diameter upper hole section defining a shoulder surface therebetween, said mouth mirror apparatus further comprising a bearing unit disposed on said shoulder surface and between said major wall and said hub to permit said hub to rotate relative to said major wall, and a fastening member having an abutment head and a threaded shank such that when said threaded shank is screwed into said rotatable shaft along the shaft axis, said abutment head is brought into abutting engagement with both said hub and said rotatable shaft to thereby permit co-rotation of said driving member and said mirror member.

8. A mouth mirror apparatus comprising:

a mounting frame defining a central axis, and including a major wall with a periphery, and a surrounding wall which has an upper wall segment which extends upwardly from said periphery to surround the central axis and to terminate at an upper end, and which defines an upper space together with said major wall, said upper wall segment having a suction port, and a lower wall segment which extends downwardly from said periphery to surround the central axis and to terminate at a lower end, and which defines a lower space together with said major wall;

an elongated handle defining therein a passage, and having a fluid outlet port downstream of said passage, said elongated handle being connected to said surrounding wall such that said passage is disposed downstream of said suction port;

a mirror member rotatably mounted on said major wall, and including a mirror body which is disposed in said upper space and which has a reflecting surface facing upwardly, and a rotatable shaft which extends downwardly from said mirror body through said major wall into said lower space so as to be driven to rotate about a shaft axis;

a driving member coupled to said rotatable shaft so as to drive said rotatable shaft to rotate about the shaft axis, wherein said driving member is rotatably disposed in said lower space and is mounted on said rotatable shaft so as to permit said rotatable shaft to rotate therewith, said driving member including a plurality of blades which are angularly displaced from one another about the shaft axis;

wherein said mounting frame further includes a bottom cover wall secured to said lower end of said lower wall segment to enclose said lower space, said lower wall segment having an internal port communicating said passage with said lower space, said mounting frame being formed with at least one fluid intake port disposed upstream of said internal port such that a fluid stream is permitted to be drawn into said lower space through said fluid intake port to flow toward said internal port so as to force said blades to rotate about the shaft axis to thereby rotate said mirror member; and wherein said elongated handle is formed with an opening which is in fluid communication with said passage, and which is disposed downstream of said internal port, said mouth mirror apparatus further comprising a gate member which is mounted on said elongated handle, and which is displaceable between a closed position, where said opening is closed by said gate member to permit generation of the fluid stream, and an open position, where said opening is unclosed to interrupt the drawing of the fluid through said fluid intake port.

9. The mouth mirror apparatus according to claim 1, wherein said elongated handle includes a tubular end portion which defines said fluid outlet port, and which has a serrated outer surface, said fluid outlet port being configured to face downwardly.

* * * * *